(12) United States Patent
Fujii et al.

(10) Patent No.: US 8,436,214 B2
(45) Date of Patent: May 7, 2013

(54) NONCRYSTALLINE FORM OF FLUORENE DERIVATIVE AND PROCESS FOR PREPARATION THEREOF

(75) Inventors: Katsuhiro Fujii, Hyogo (JP); Suguru Hata, Hyogo (JP); Kohta Fukui, Chiba (JP)

(73) Assignee: Taoka Chemcial Co., Ltd., Osaka (JP)

( * ) Notice: Subject to any disclaimer, the term of this patent is extended or adjusted under 35 U.S.C. 154(b) by 40 days.

(21) Appl. No.: 13/376,516

(22) PCT Filed: Jun. 1, 2010

(86) PCT No.: PCT/JP2010/059245
§ 371 (c)(1),
(2), (4) Date: Dec. 6, 2011

(87) PCT Pub. No.: WO2010/143556
PCT Pub. Date: Dec. 16, 2010

(65) Prior Publication Data
US 2012/0095270 A1    Apr. 19, 2012

(30) Foreign Application Priority Data

Jun. 11, 2009 (JP) ................................. 2009-139852
Jun. 25, 2009 (JP) ................................. 2009-150786

(51) Int. Cl.
*C07C 41/40* (2006.01)
*C07C 43/23* (2006.01)

(52) U.S. Cl.
USPC ........................................................ 568/633

(58) Field of Classification Search ................... 568/633
See application file for complete search history.

(56) References Cited

U.S. PATENT DOCUMENTS

| 5,629,456 A | 5/1997 | Yamada et al. |
| 2010/0105961 A1 | 4/2010 | Fujii et al. |

FOREIGN PATENT DOCUMENTS

| JP | 7-165657 A | 6/1995 |
| JP | 10-045654 A | 2/1998 |
| JP | 11-158106 A | 6/1999 |
| JP | 2004-339499 A | 12/2004 |
| JP | 2005-104898 A | 4/2005 |
| JP | 2007-023016 A | 2/2007 |
| JP | 2007-197368 A | 8/2007 |
| JP | 4140975 B1 | 6/2008 |
| JP | 2008-222708 A | 9/2008 |

OTHER PUBLICATIONS

International Search Report for corresponding International Application No. PCT/JP2010/059245 mailed Jul. 6, 2010.
Form PCT/ISA/237 for corresponding International Application No. PCT/JP2010/059245 dated Jul. 6, 2010.
Sun et al., "Studies on the Formation of Novel Copolyesters Containing Naphthalene and Aralkyloxy Structures", J. of Applied Polymer Science, 1995, vol. 58, pp. 1189-1197.

*Primary Examiner* — Sikarl Witherspoon
(74) *Attorney, Agent, or Firm* — Renner, Otto, Boisselle & Sklar, LLP

(57) ABSTRACT

An object of the present invention is to provide (i) a novel non-crystalline form of 9,9-bis(4-(2-hydroxyethoxy) phenyl) fluorene, which non-crystalline form maintains quality at a certain level, and is excellent as a polymer material, and (ii) a method of preparing the non-crystalline form. According to the present invention, molten 9,9-bis(4-(2-hydroxyethoxy) phenyl) fluorene in a liquid form is cooled and therefore is solidified. With the method, it is possible to provide a novel non-crystalline form of 9,9-bis(4-(2-hydroxyethoxy) phenyl) fluorene which has a small risk that powder dust of 9,9-bis(4-(2-hydroxyethoxy) phenyl) fluorine might cause explosion or a health problem. Further, the non-crystalline form of 9,9-bis (4-(2-hydroxyethoxy) phenyl) fluorene can be adjusted arbitrarily in particle diameter by, for example, pulverizing the non-crystalline form in accordance with equipment or usage. In other words, the non-crystalline form of 9,9-bis(4-(2-hydroxyethoxy) phenyl) fluorene is advantageous in handleability industrially.

15 Claims, 3 Drawing Sheets

NONCRYSTALLINE FORM OF FLUORENE DERIVATIVE AND PROCESS FOR PREPARATION THEREOF

TECHNICAL FIELD

The present invention relates to (i) a non-crystalline form of 9,9-bis(4-(2-hydroxyethoxy)phenyl)fluorene and (ii) a method of preparing the non-crystalline form.

BACKGROUND ART

A fluorene derivative such as 9,9-bis(4-(2-hydroxyethoxy)phenyl)fluorene shows promise as a material for production of a polymer having a high heat resistance, a high transparency, and a high index of refraction (such as epoxy resin, polyester, polyether, and polycarbonate). In recent years, the fluorene derivative has been expected to be used as a raw material of an optical lens, a film, a plastic optical fiber, an optical disc substrate, a heat-resistant resin, and an engineering plastic etc.

In order to produce stably polymers which are excellent thermally and optically in these applications, the following conditions are important, for example: (i) a molecular weight and molecular weight distribution are controllable, and (ii) a content ratio of un-reacted monomers and/or a content ratio of un-reacted oligomers is low. Further, it is desirable that 9,9-bis(4-(2-hydroxyethoxy)phenyl)fluorene monomer, serving as a raw material, (i) maintains constant physical properties, (ii) has high purity, and (iii) has high reactivity. Meanwhile, a certain sort of a solid has a polymorph which is represented by a certain chemical formula but has a plurality of different crystal structures. A pseudo-polymorph and a non-crystalline form are regarded as a sort of polymorph. Such polymorphs are different from each other in physical properties (such as density, a melting point, and solubility), and have a significant influence on physical properties of resultant polymers, and/or reactivity, which polymers are obtained with the use of the polymorphs. Accordingly, controlling a crystalline form of a raw material is one of important factors in realizing a more excellent polymer. For this reason, a lot of effort has been made to (i) find a specific crystalline form or a specific non-crystalline form and (ii) prepare such a specific form.

Further, a non-crystalline solid has transparency, homogeneity, isotropy, and excellent workability. Such a non-crystalline solid shows promise as a photonics material such as an organic electroluminescence element, a recording element, a storage element, an electrical field sensor, and an optical sampling oscilloscope. Particularly, a non-crystalline low-molecular-weight organic compound has attracted attention in recent years as a resist material having high resolution and low roughness. However, unlike a high-molecular-weight compound, a low-molecular-weight organic compound is in general highly likely to be crystallized and unlikely to have a non-crystalline form. Such a low-molecular-weight organic compound is generally in a form of crystals at a temperature equal to or lower than its melting point. The non-crystalline form may be seen, for example, in a medical product that has a complex structure. However, the non-crystalline form is thermodynamically in a nonequilibrium state and is unstable as compared with a crystalline form. Accordingly, the non-crystalline form is easily subjected to transition, so that recrystallization occurs. Therefore, finding a non-crystalline low-molecular-weight organic compound which can easily form a stable glass state is significantly important, even in terms of creating a new functional material which is different from a conventional non-crystalline polymer or a conventional polymer composite material.

Examples of a method of producing 9,9-bis(4-(2-hydroxyethoxy)phenyl)fluorene encompass a method of causing fluorenone and phenoxyethanol to be subjected to dehydration condensation, by use of sulfuric acid and thiols as catalysts (Patent Literature 1), and a method of causing 9,9-bis(4-hydroxyphenyl)fluorene and ethylene carbonate to react with each other (Non-Patent Literature 1). Further, we made a patent application of a novel production method (Patent Literature 2), which is different from the methods described above.

Moreover, as a crystalline form of 9,9-bis(4-(2-hydroxyethoxy)phenyl)fluorene, Patent Literature 3 discloses that there is a polymorph (hereinafter, referred to as "polymorph B") having a melting point in a range of 150° C. to 180° C., other than a polymorph (hereinafter, referred to as "polymorph A") having a melting point in a range of 100° C. to 130° C., which polymorph A has been conventionally known. However, it has not been known that there is another crystalline form or a non-crystalline form of 9,9-bis(4-(2-hydroxyethoxy)phenyl)fluorene, other than the above two sorts of polymorph.

Citation List

[Patent Literature]

[Patent Literature 1]

Japanese Patent Application Publication, Tokukaihei, No. 7-165657 A (1995) (Publication Date: Jun. 27, 1995)

[Patent Literature 2]

Japanese Patent Application Publication, Tokukai, No. 2007-23016 A (Publication Date: Feb. 1, 2007)

[Patent Literature 3]

Japanese Patent No. 4140975 B (Publication Date: Jun. 20, 2008)

[Non-Patent Literature]

[Non-Patent Literature 1]

Journal of Applied Polymer Science, 1995, Vol. 58, 1189-1197

SUMMARY OF INVENTION

Technical Problem

An object of the present invention is to provide (i) a novel non-crystalline form of 9,9-bis(4-(2-hydroxyethoxy)phenyl)fluorene, which non-crystalline form (I) can maintain quality at a certain level, (II) is excellent as a raw material of a polymer, and (III) is useful as a novel functional material, e.g., an optical material or a photonics material, and (ii) a method of preparing the non-crystalline form.

Solution to Problem

The inventors of the present invention found, as a result of diligent study in view of the problems described above, that, other than the two sorts of crystalline form (i.e., polymorphs A and B), there is a non-crystalline form of 9,9-bis(4-(2-hydroxyethoxy)phenyl)fluorene, i.e., a non-crystalline solid of 9,9-bis(4-(2-hydroxyethoxy)phenyl)fluorene. Further, the inventors of the present invention realized the present invention by finding a method of producing such a non-crystalline form selectively.

That is, the present invention provides the following (1) through (6).

(1) Non-crystalline 9,9-bis(4-(2-hydroxyethoxy)phenyl)fluorene (i.e., a non-crystalline form (non-crystalline solid) of 9,9-bis(4-(2-hydroxyethoxy)phenyl)fluorene).

(2) A non-crystalline form of 9,9-bis(4-(2-hydroxyethoxy)phenyl)fluorene described in (1), wherein an X-ray powder diffraction pattern of the non-crystalline form has no sharp peak and has a halo pattern at a diffraction angle in a range of 5° to 60°.

(3) A non-crystalline form of 9,9-bis(4-(2-hydroxyethoxy)phenyl)fluorene, wherein: an X-ray diffraction peak pattern has a broad halo pattern at 2θ in a range of approximately 5° to approximately 30'; and a differential scanning calorimetry thermogram has no endothermic peak at approximately 161° C. and no endothermic peak at approximately 119° C., each of which endothermic peaks is inherent in a crystalline form of 9,9-bis(4-(2-hydroxyethoxy)phenyl)fluorene.

(4) A method of producing a non-crystalline form of 9,9-bis(4-(2-hydroxyethoxy)phenyl)fluorene, the method including the step of: solidifying molten 9,9-bis(4-(2-hydroxyethoxy)phenyl)fluorene in a liquid form by cooling the molten 9,9-bis(4-(2-hydroxyethoxy)phenyl)fluorene.

(5) The method described in the above (4), wherein: the molten 9,9-bis(4-(2-hydroxyethoxy)phenyl)fluorene in the liquid form is obtained in such a manner that 9,9-bis(4-(2-hydroxyethoxy)phenyl)fluorene is subjected to a distillation process.

(6) The method described in the above (4) or (5), wherein: the molten 9,9-bis(4-(2-hydroxyethoxy)phenyl)fluorene is produced in such a manner that 9,9-bis(4-(2-hydroxyethoxy)phenyl)fluorene is heated at a temperature in a range of 100° C. to 400° C.

Advantageous Effects of Invention

According to the present invention, it is possible to provide a novel non-crystalline form of 9,9-bis(4-(2-hydroxyethoxy)phenyl)fluorene, and a method of producing the novel non-crystalline form. Further, unlike the known polymorphs A and B which are crystals in a powder form, the non-crystalline form of the present invention is a glassy material. Accordingly, with the non-crystalline form of the present invention, there is a less risk that powder dust of 9,9-bis(4-(2-hydroxyethoxy)phenyl)fluorene might cause explosion or a health problem. Further, it is possible to adjust arbitrarily a particle size of the non-crystalline form of the present invention by, for example, pulverizing the non-crystalline form in accordance with equipment or usage. Accordingly, the non-crystalline form of the present invention is advantageous in handleability industrially.

Further, since the crystalline polymorphs A and B are in the powder form, they have a problem that, when absorbing water, they are likely to be gathered together into a mass. On the other hand, the non-crystalline form of the present invention is a glassy material. Accordingly, the non-crystalline form of the present invention is excellent in handleability without the above problem.

Furthermore, with the non-crystalline form of the present invention, transition is not likely to occur. That is, recrystallization is not likely to occur. That is, the non-crystalline form is a glassy material which is excellent in stability and transparency, and is useful as a novel functional material, e.g., an optical material or a photonics material.

DESCRIPTION OF EMBODIMENTS

Generally, a non-crystalline solid is made of a random molecular arrangement, and has no distinguishable crystal lattice. Further, generally, the non-crystalline solid is higher than a crystalline form in solubility, and has no constant melting point. Accordingly, a non-crystalline form is confirmed by a fact that (i) no distinct peak is found in an X-ray powder diffraction pattern and (ii) no melting endothermic peak is found in a differential scanning calorimetry (DSC) curve.

A non-crystalline form of the present invention has at least one of the following features (a) through (d).

Figure 1:
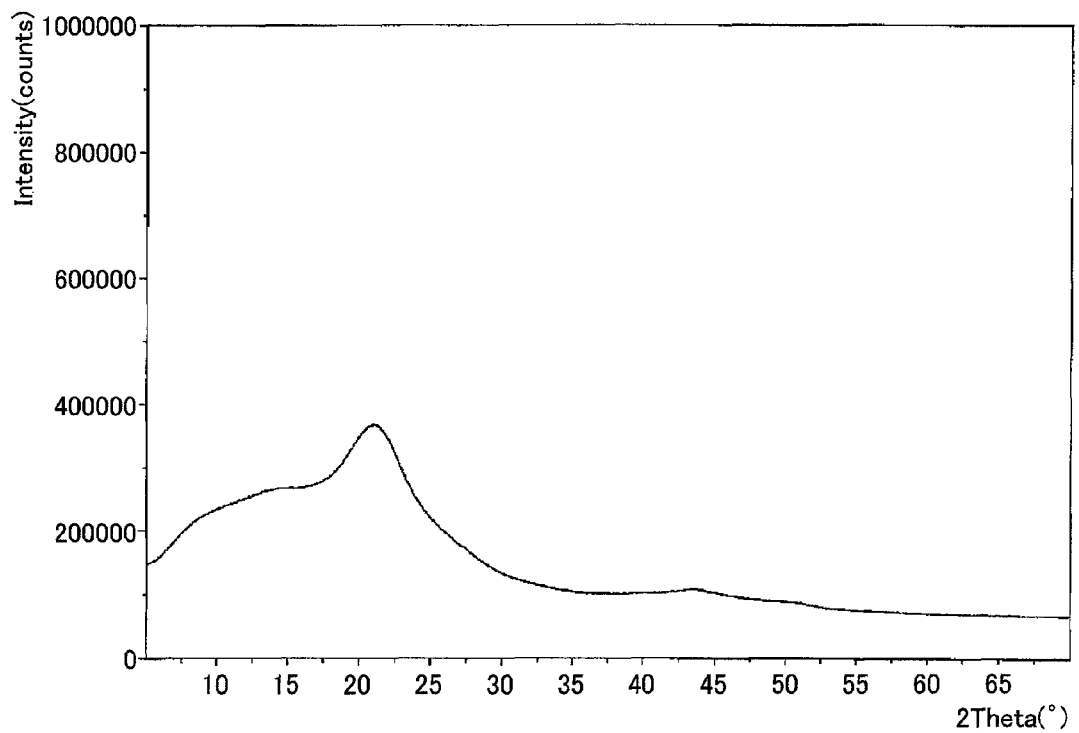
FIG. 1 is a view showing a characteristic X-ray powder diffraction pattern of a non-crystalline form of 9,9-bis(4-(2-hydroxyethoxy)phenyl)fluorene.

(a) The non-crystalline form of 9,9-bis(4-(2-hydroxyethoxy)phenyl)fluorene in accordance with the present invention has an X-ray powder diffraction pattern which (i) has no sharp peak which is a feature of a crystalline form and (ii) has a broad peak (halo pattern) at a diffraction angle (2θ) in a range of approximately 5° to approximately 60°, which broad peak is a typical feature of the non-crystalline form. More specifically, the non-crystalline form of the present invention has an X-ray powder diffraction pattern which is substantially identical with a pattern shown in FIG. 1.

(b) The non-crystalline form of 9,9-bis(4-(2-hydroxyethoxy)phenyl)fluorene in accordance with the present invention has (I) an X-ray diffraction pattern which has a broad halo pattern at 2θ in a range of approximately 5° to approximately 30°, and (II) a differential scanning calorimetry (DSC) thermogram has no endothermic peak at approximately 161° C. and no endothermic peak at approximately 119° C., each of which endothermic peaks is inherent in a crystalline form of 9,9-bis(4-(2-hydroxyethoxy)phenyl)fluorene. Note, here, that, as to the crystalline form of 9,9-bis(4-(2-hydroxyethoxy)phenyl)fluorene, there are two crystalline forms, i.e., polymorphs A and B (as disclosed in Japanese Patent No. 4140975 B). The polymorph A has, in a differential scanning calorimetry thermogram, an endothermic peak at a temperature in a range of 100° C. to 130° C., while the polymorph B has, in a differential scanning calorimetry thermogram, an endothermic peak at a temperature in a range of 150° C. to 180° C. Accordingly, the aforementioned (II) the differential scanning calorimetry (DSC) thermogram is not limited to the one which has no endothermic peak at approximately 161° C. and no endothermic peak at approximately 119° C., but also includes a differential scanning calorimetry (DSC) thermogram which has no endothermic peak at any temperature in a range of 150° C. to 180° C. and no endothermic peak at any temperature in a range of 100° C. to 130° C., which endothermic peaks are inherent in the respective two crystalline forms of 9,9-bis(4-(2-hydroxyethoxy)phenyl)fluorene.

Figure 2:
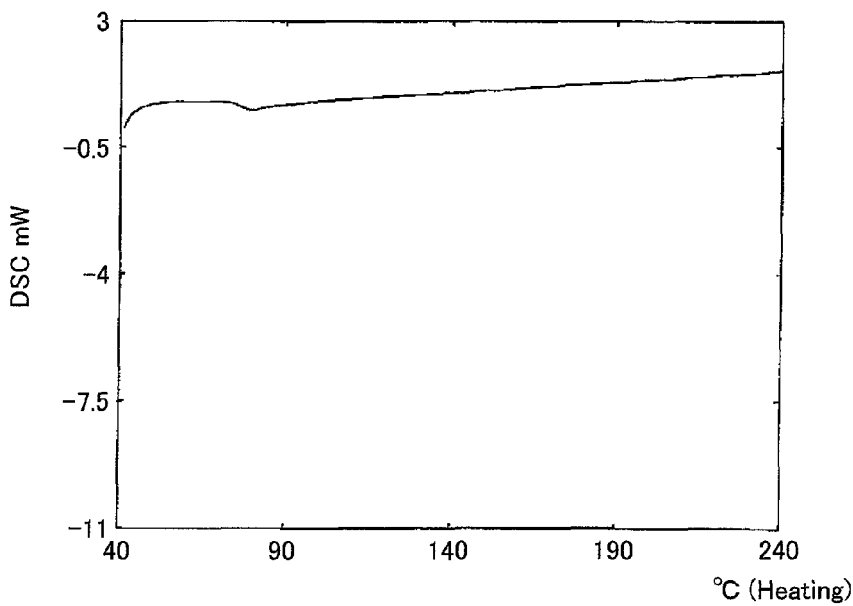
FIG. 2 is a view showing a characteristic differential scanning calorimetry (DSC) curve of the non-crystalline form of 9,9-bis(4-(2-hydroxyethoxy)phenyl)fluorene.

(c) The non-crystalline form of 9,9-bis(4-(2-hydroxyethoxy)phenyl)fluorene in accordance with the present invention has a differential scanning calorimetry (DSC) curve which has no distinct melting endothermic peak related to first-order transition, such as a melting point of a crystal. More specifically, the non-crystalline form of the present invention has a DSC curve which is substantially identical with a DSC curve shown in FIG. 2.

(d) The non-crystalline form of 9,9-bis(4-(2-hydroxyethoxy)phenyl)fluorene in accordance with the present invention is a transparent glassy solid, which can be recognized visually.

According to the present invention, an X-ray powder diffraction pattern was measured by use of an X-ray diffractometer (X' PertPRO, manufactured by Spectris Co., Ltd.) having a Cu X-ray source, which operates with a voltage of 45 kV and a current of 40 mA. In the measurement, a sample was rotated at 120 rpm, while it is analyzed at an angle (θ to 2θ) in a range of 5° to 70° and at a speed of 2.0°/minute.

According to the present invention, a differential scanning calorimetry (DSC) curve was measured by use of a differential scanning calorimeter (DSC220C, manufactured by Seiko Instruments Inc.). A sample was precisely measured and put on an aluminum pan. Then, the sample was purged by use of a nitrogen gas at a flow rate of 40 ml/minute. The scanning was carried out at a temperature in a range of 40° C. to 260° C. and at a scanning speed of 10° C./minute.

It is clear for a person skilled in the art that, in the measurement of the X-ray powder diffraction pattern and the differential scanning calorimetry (DSC) curve, an experimental error might occur due to a device, adjustment of a sample, or other causes. Accordingly, in a case where the present specification includes such a description that a form of a solid of the present invention shows an X-ray powder diffraction pattern which is substantially identical with a pattern shown in a certain figure, or such a description that a form of a solid of the present invention shows a DSC curve which is substantially identical with a DSC curve shown in a certain figure, the wording "substantially identical" includes such an experimental error.

The non-crystalline form of 9,9-bis(4-(2-hydroxyethoxy)phenyl)fluorene in accordance with the present invention may be a solid having a single non-crystalline form. Alternatively, the non-crystalline form of the present invention may be a solid having a crystalline form or another non-crystalline form of the same 9,9-bis(4-(2-hydroxyethoxy)phenyl)fluorene, in an amount of less than 20% by weight, preferably less than 10% by weight, more preferably less than 3% by weight, most preferably less than 1% by weight. In other words, the non-crystalline form of 9,9-bis(4-(2-hydroxyethoxy)phenyl)fluorene in accordance with the present invention can be made from only the non-crystalline form of 9,9-bis(4-(2-hydroxyethoxy)phenyl)fluorene or can contain a crystalline form or another non-crystalline form in an amount in the aforementioned range. Further, the non-crystalline form of 9,9-bis(4-(2-hydroxyethoxy)phenyl)fluorene in accordance with the present invention can contain at least one of a crystalline form and another non-crystalline form in an amount in the aforementioned range.

The non-crystalline form of 9,9-bis(4-(2-hydroxyethoxy)phenyl)fluorene in accordance with the present invention can be obtained by solidifying molten 9,9-bis(4-(2-hydroxyethoxy)phenyl)fluorene in a liquid form by cooling the molten 9,9-bis(4-(2-hydroxyethoxy)phenyl)fluorene. The cooling does not cause 9,9-bis(4-(2-hydroxyethoxy)phenyl)fluorene to be crystallized.

According to the present invention, the term "molten" means a state of a material, which state is such that (i) a material is heated at a melting point or higher temperatures, or at a temperature not lower than a temperature at which the material starts to be distorted, and therefore (ii) the material becomes in the liquid form.

How to prepare the molten material in the liquid form is not particularly limited. For example, a crystal of 9,9-bis(4-(2-hydroxyethoxy)phenyl)fluorene is heated so as to be molten. Further, the molten material can be also obtained in such a manner that (i) 9,9-bis(4-(2-hydroxyethoxy)phenyl)fluorene is dissolved in a suitable solvent, and (ii) a resultant solution is subjected to distillation so that the solvent is removed from the solution. Furthermore, the molten material can be obtained in such a manner that (i) 9,9-bis(4-(2-hydroxyethoxy)phenyl)fluorene is subjected to reduced-pressure distillation at a temperature of not less than a melting point, and (ii) a resultant molten material is collected.

In a case where a crystal is molten, the crystalline form of 9,9-bis(4-(2-hydroxyethoxy)phenyl)fluorene is not particularly limited, and may be one of the polymorphs A and B, or a mixture of these. These polymorphs would not be recrystallized through a cooling process for causing the molten material to be solidified. Further, these polymorphs would not be recrystallized even if they are heated again.

A temperature at which the molten material is prepared is not particularly limited, provided that it is not less than a temperature at which 9,9-bis(4-(2-hydroxyethoxy)phenyl)fluorene starts to be molten. Note, however, that such a temperature is generally in a range of 100° C. to 400° C., preferably in a range of 150° C. to 350° C., more preferably in a range of 170° C. to 250° C. A temperature higher than the above range is not suitable to prepare the molten material. This is because, in a case where 9,9-bis(4-(2-hydroxyethoxy)phenyl)fluorene is heated at a temperature higher than the above range, it might be decomposed.

Moreover, a temperature at which 9,9-bis(4-(2-hydroxyethoxy)phenyl)fluorene is subjected to reduced-pressure distillation is preferably in a range of 170° C. to 400° C., more preferably in a range of 200° C. to 350° C.

It is possible to cool the molten material thus obtained immediately after the molten material is prepared. However, it is preferable to cool the molten material after the molten material is stirred for a predetermined time period (for example, 30 minutes or longer).

A temperature at which the molten material is cooled is not particularly limited, provided that it is lower than a temperature at which 9,9-bis(4-(2-hydroxyethoxy)phenyl)fluorene starts to be solidified. Such a temperature is preferably not higher than 150° C., more preferably not higher than 100° C. Generally, the molten material is cooled to room temperature (approximately 25° C.).

A cooling rate at which the molten material is cooled is not particularly limited. A solid having the non-crystalline form can be obtained either at a low cooling rate (e.g., cooling rate: 0.2° C./minute) or at a high cooling rate (e.g., cooling rate: 10° C./minute). It is preferable that the cooling rate is in a range of 0.5° C. to 10° C./minute, more preferably in a range of 2° C. to 10° C./minute.

How to produce 9,9-bis(4-(2-hydroxyethoxy)phenyl)fluorene which is to be molten 9,9-bis(4-(2-hydroxyethoxy)phenyl)fluorene in the liquid form is not particularly limited. It is preferable to produce 9,9-bis(4-(2-hydroxyethoxy)phenyl)fluorene by causing fluorenone and 2-phenoxyethanol to be reacted with each other under the presence of an acid catalyst. It is more preferable to produce 9,9-bis(4-(2-hydroxyethoxy)phenyl)fluorene by causing fluorenone and 2-phenoxyethanol to be reacted with each other under the presence of a heteropoly acid catalyst (such as phosphomolybdic acid, phosphotungstic acid, silicomolybdic acid, silicotungstic acid, and phosphovanadomolybdic acid). Further, the polymorph B can be obtained by a method described in the specification of Japanese Patent No. 4140975 B, for example.

EXAMPLES

The present invention is described below more specifically with Examples. Note, however, that the present invention is not limited to the Examples.

Example 1

A polymorph B of 9,9-bis(4-(2-hydroxyethoxy)phenyl) fluorene was obtained in accordance with a method described in Example 2 of the specification of Japanese Patent No. 4140975 B. The polymorph B thus obtained was put in a flask made from glass, and was heated at 230° C. Molten 9,9-bis (4-(2-hydroxyethoxy)phenyl)fluorene in a liquid form was thus obtained. The molten 9,9-bis(4-(2-hydroxyethoxy)phenyl)fluorene was further heated at 230° C. for 1 hour. The molten 9,9-bis(4-(2-hydroxyethoxy)phenyl)fluorene was cooled to room temperature for approximately 4 hours, so that a transparent and colorless glassy solid was obtained. An X-ray powder diffraction pattern of the glassy solid (9,9-bis (4-(2-hydroxyethoxy)phenyl)fluorene) thus obtained showed a feature which was identical with a feature shown in FIG. 1. A DSC curve of the glassy solid (9,9-bis(4-(2-hydroxyethoxy)phenyl)fluorene) thus obtained showed a feature which was identical with a feature shown in FIG. 2. That is, the glassy solid (9,9-bis(4-(2-hydroxyethoxy)phenyl)fluorene) thus obtained had a non-crystalline form.

Example 2

A polymorph A of 9,9-bis(4-(2-hydroxyethoxy)phenyl) fluorene was obtained in accordance with a method described in Comparative Example 1 in the specification of Japanese Patent No. 4140975 B. The polymorph A thus obtained was supplied to a Kugelrohr distillation apparatus, and was subjected to reduced-pressure distillation at 300° C. Molten 9,9-bis(4-(2-hydroxyethoxy)phenyl)fluorene in a liquid form was thus collected. The molten 9,9-bis(4-(2-hydroxyethoxy)phenyl)fluorene in the liquid form was cooled to room temperature for approximately 10 hours. A transparent and colorless glassy solid was thus obtained. An X-ray powder diffraction pattern of the glassy solid (9,9-bis(4-(2-hydroxyethoxy)phenyl)fluorene) thus obtained showed a feature which was identical with a feature shown in FIG. 1. A DSC curve of the glassy solid (9,9-bis(4-(2-hydroxyethoxy)phenyl)fluorene) thus obtained showed a feature which was identical with a feature shown in FIG. 2. That is, the glassy solid (9,9-bis(4-(2-hydroxyethoxy)phenyl)fluorene) thus obtained had a non-crystalline form.

Comparative Example 1

Figure 3:
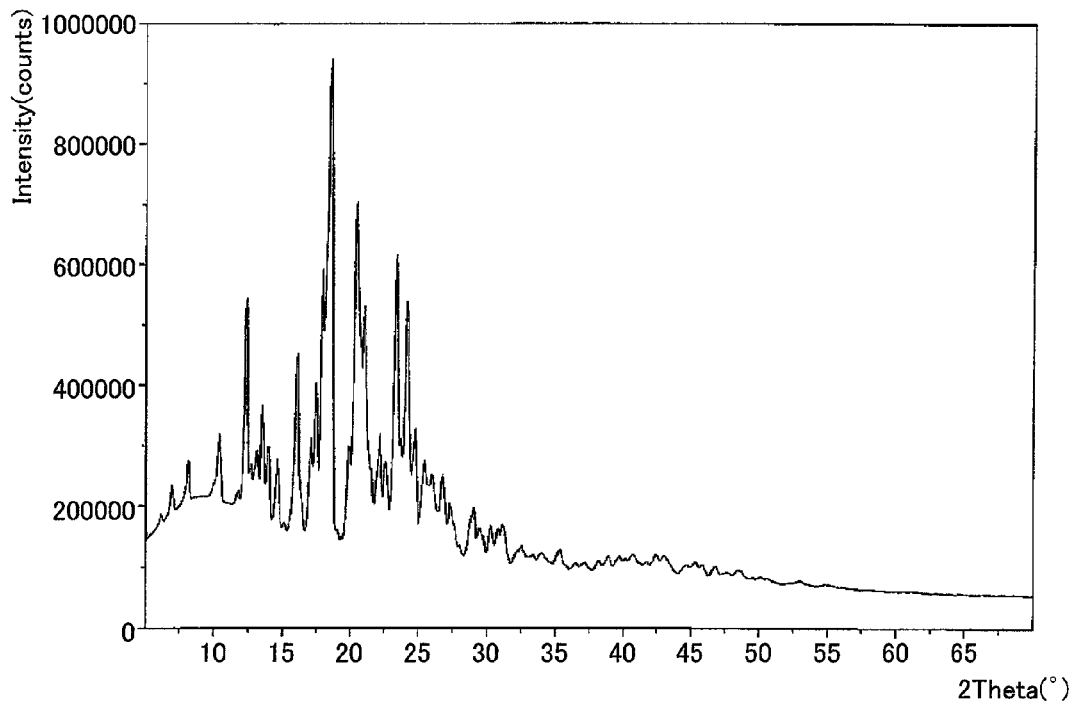
FIG. 3 is a view showing a characteristic X-ray powder diffraction pattern of a polymorph B of 9,9-bis(4-(2-hydroxyethoxy)phenyl)fluorene.
Figure 4:
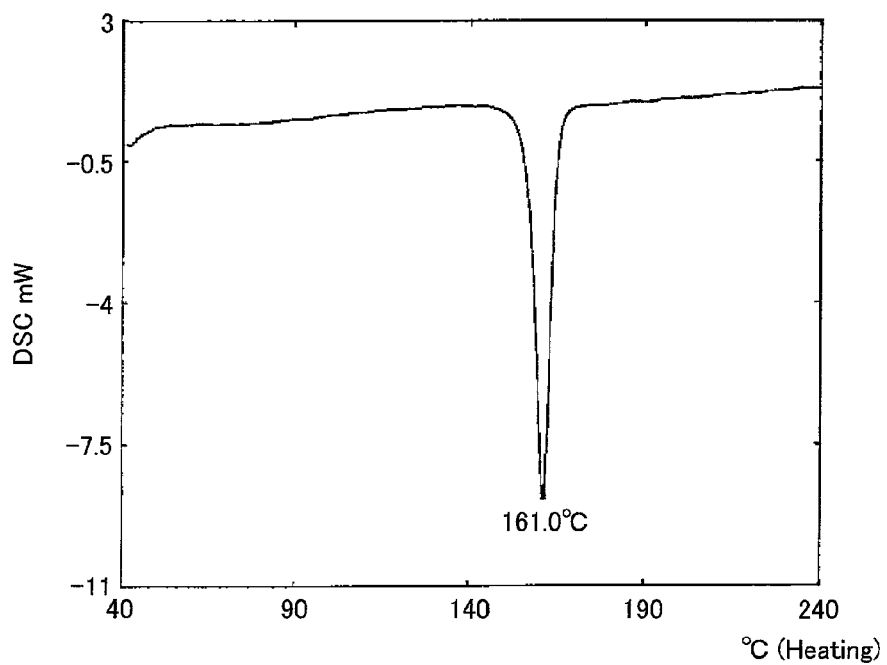
FIG. 4 is a view showing a characteristic differential scanning calorimetry (DSC) curve of the polymorph B of 9,9-bis(4-(2-hydroxyethoxy)phenyl)fluorene.

A polymorph B of 9,9-bis(4-(2-hydroxyethoxy)phenyl) fluorene was obtained as a white crystal in accordance with a method described in Example 2 of the specification of Japanese Patent No. 4140975 B. FIG. 3 shows an X-ray powder diffraction pattern of the polymorph B thus obtained. FIG. 4 shows a DSC curve of the polymorph B thus obtained.

Comparative Example 2

Figure 5:
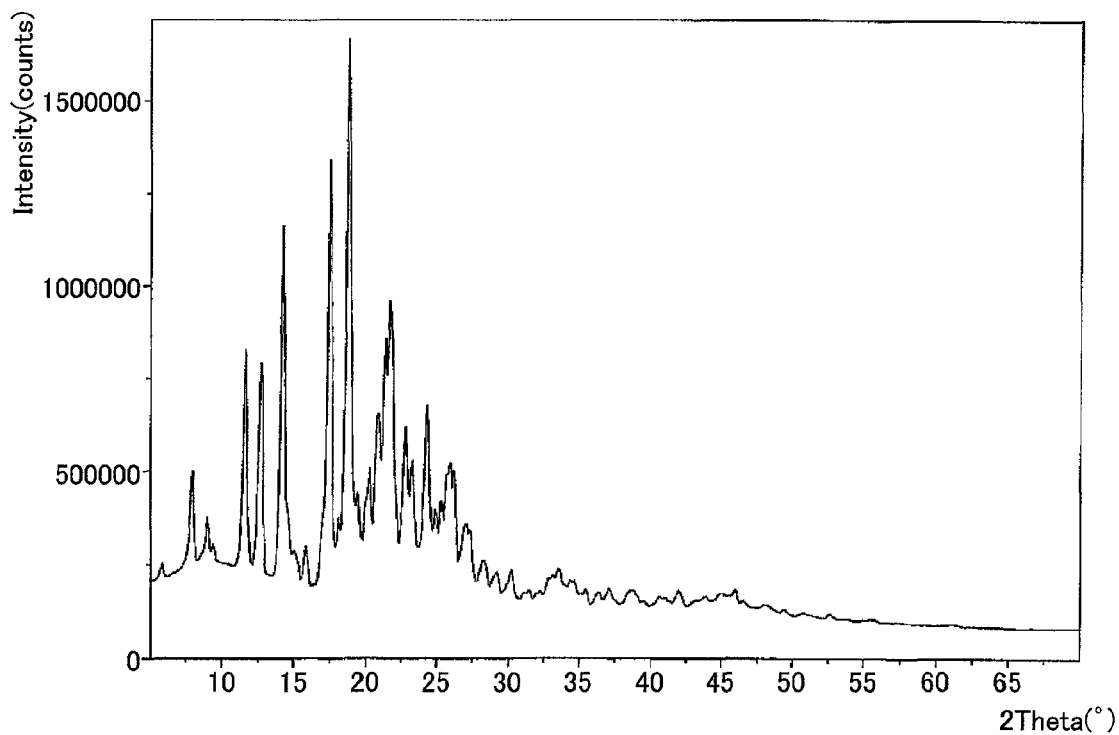
FIG. 5 is a view showing a characteristic X-ray powder diffraction pattern of a polymorph A of 9,9-bis(4-(2-hydroxyethoxy)phenyl)fluorene.
Figure 6:
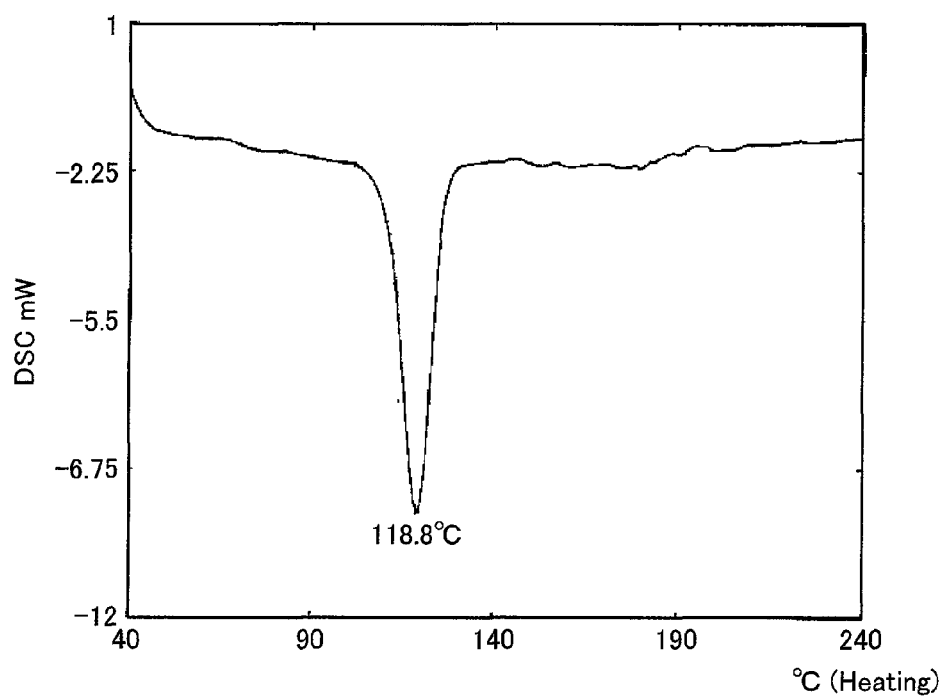
FIG. 6 is a view showing a characteristic differential scanning calorimetry (DSC) curve of the polymorph A of 9,9-bis(4-(2-hydroxyethoxy)phenyl)fluorene.

A polymorph A of 9,9-bis(4-(2-hydroxyethoxy)phenyl) fluorene was obtained as a white crystal in accordance with a method described in Comparative Example 1 of the specification of Japanese Patent No. 4140975 B. FIG. 5 shows an X-ray diffraction pattern of the polymorph A thus obtained. FIG. 6 shows a DSC curve of the polymorph A thus obtained.

Industrial Applicability

According to the present invention, it is possible to provide novel non-crystalline form of 9,9-bis(4-(2-hydroxyethoxy) phenyl)fluorene, and a method of producing the novel non-crystalline form. Further, unlike known polymorphs A and B which are crystals in a powder form, the non-crystalline form of the present invention is a glassy material. For this reason, the non-crystalline form obtained in accordance with the present invention has a small risk that powder dust of 9,9-bis (4-(2-hydroxyethoxy)phenyl)fluorene might cause explosion or a health problem. Further, it is possible to adjust arbitrarily a particle size of the non-crystalline form obtained in accordance with the present invention by, for example, pulverizing the non-crystalline form in accordance with equipment or usage. That is, the non-crystalline form obtained in accordance with the present invention is advantageous in handleability industrially. Furthermore, the non-crystalline form obtained in accordance with the present invention is a glassy material which is excellent in transparency, and therefore is useful as a novel functional material such as an optical material or photonics material.

Accordingly, the non-crystalline form of 9,9-bis(4-(2-hydroxyethoxy)phenyl)fluorene in accordance with the present invention is useful as a raw material of a polymer, and can be used as a raw material of an epoxy resin, polyester, polyether, or polycarbonate.

The invention claimed is:

1. A non-crystalline form of 9,9-bis(4-(2-hydroxyethoxy) phenyl) fluorene.

2. The non-crystalline form as set forth in claim 1, wherein:
an X-ray powder diffraction pattern of the non-crystalline form has no sharp peak, and has a halo pattern at a diffraction angle in a range of 5° to 60°.

3. A non-crystalline form of 9,9-bis(4-(2-hydroxyethoxy) phenyl) fluorene, wherein:
an X-ray diffraction peak pattern of the non-crystalline form has a broad halo pattern at 2θ in a range of approximately 5° to approximately 30°; and
a differential scanning calorimetry thermogram of the non-crystalline form has no endothermic peak at approximately 161° C. and no endothermic peak at approximately 119° C., each of the endothermic peaks being inherent in a crystalline form of 9,9-bis(4-(2-hydroxyethoxy) phenyl) fluorene.

4. A method of producing a non-crystalline form of 9,9-bis (4-(2-hydroxyethoxy) phenyl) fluorene, the non-crystalline form being recited in claim 1, the method comprising the step of:
solidifying molten 9,9-bis(4-(2-hydroxyethoxy) phenyl) fluorene in a liquid form by cooling the molten 9,9-bis (4-(2-hydroxyethoxy) phenyl) fluorene.

5. The method as set forth in claim 4, wherein:
the molten 9,9-bis(4-(2-hydroxyethoxy) phenyl) fluorene in the liquid form is obtained in such a manner that 9,9-bis(4-(2-hydroxyethoxy) phenyl) fluorene is subjected to a distillation process.

6. The method as set forth in claim 4, wherein:
the molten 9,9-bis(4-(2-hydroxyethoxy) phenyl) fluorene is produced in such a manner that 9,9-bis(4-(2-hydroxyethoxy) phenyl) fluorene is heated at a temperature in a range of 100° C. to 400° C.

7. The method as set forth in claim 5, wherein:
the molten 9,9-bis(4-(2-hydroxyethoxy) phenyl) fluorene is produced in such a manner that 9,9-bis(4-(2-hydroxyethoxy) phenyl) fluorene is heated at a temperature in a range of 100° C. to 400° C.

8. A method of producing a non-crystalline form of 9,9-bis (4-(2-hydroxyethoxy) phenyl) fluorene, the non-crystalline form being recited in claim 2, the method comprising the step of:
solidifying molten 9,9-bis(4-(2-hydroxyethoxy) phenyl) fluorene in a liquid form by cooling the molten 9,9-bis (4-(2-hydroxyethoxy) phenyl) fluorene.

9. The method as set forth in claim 8, wherein:
the molten 9,9-bis(4-(2-hydroxyethoxy) phenyl) fluorene in the liquid form is obtained in such a manner that 9,9-bis(4-(2-hydroxyethoxy) phenyl) fluorene is subjected to a distillation process.

10. The method as set forth in claim 8, wherein:
the molten 9,9-bis(4-(2-hydroxyethoxy) phenyl) fluorene is produced in such a manner that 9,9-bis(4-(2-hydroxyethoxy) phenyl) fluorene is heated at a temperature in a range of 100° C. to 400° C.

11. The method as set forth in claim 9, wherein:
the molten 9,9-bis(4-(2-hydroxyethoxy) phenyl) fluorene is produced in such a manner that 9,9-bis(4-(2-hydroxyethoxy) phenyl) fluorene is heated at a temperature in a range of 100° C. to 400° C.

12. A method of producing a non-crystalline form of 9,9-bis(4-(2-hydroxyethoxy) phenyl) fluorene, the non-crystalline form being recited in claim 3, the method comprising the step of:
solidifying molten 9,9-bis(4-(2-hydroxyethoxy) phenyl) fluorene in a liquid form by cooling the molten 9,9-bis (4-(2-hydroxyethoxy) phenyl) fluorene.

13. The method as set forth in claim 12, wherein:
the molten 9,9-bis(4-(2-hydroxyethoxy) phenyl) fluorene in the liquid form is obtained in such a manner that 9,9-bis(4-(2-hydroxyethoxy) phenyl) fluorene is subjected to a distillation process.

14. The method as set forth in claim 12, wherein:
the molten 9,9-bis(4-(2-hydroxyethoxy) phenyl) fluorene is produced in such a manner that 9,9-bis(4-(2-hydroxyethoxy) phenyl) fluorene is heated at a temperature in a range of 100° C. to 400° C.

15. The method as set forth in claim 13, wherein:
the molten 9,9-bis(4-(2-hydroxyethoxy) phenyl) fluorene is produced in such a manner that 9,9-bis(4-(2-hydroxyethoxy) phenyl) fluorene is heated at a temperature in a range of 100° C. to 400° C.

* * * * *